United States Patent [19]

Oda et al.

[11] Patent Number: 5,114,466

[45] Date of Patent: May 19, 1992

[54] 1-(3-SUBSTITUTED BENZYL)-3-HALOGENO-4-(1-HALOGENO-ALKYL)-2-PYRROLIDINONE DERIVATIVES AND HERBICIDES CONTAINING THEM

[75] Inventors: Kengo Oda; Koichi Moriyasu; Masao Hayashi; Makoto Nishida; Masami Oyamada; Akie Fujiwara, all of Mobara; Junko Watanabe, Tokyo, all of Japan

[73] Assignee: Mitsui Toatsu Chemicals, Inc., Tokyo, Japan

[21] Appl. No.: 534,060

[22] Filed: Jun. 6, 1990

[30] Foreign Application Priority Data

Jun. 14, 1989 [JP] Japan ................ 1-149516

[51] Int. Cl.⁵ .................. C07D 207/38; A01N 43/36
[52] U.S. Cl. ...................... 71/94; 548/543; 548/550; 548/551
[58] Field of Search .............. 548/543; 71/94

[56] References Cited

U.S. PATENT DOCUMENTS

| 4,110,105 | 8/1978 | Teach | 548/543 |
| 4,210,589 | 7/1980 | Teach | 548/543 |
| 4,645,843 | 2/1987 | Broadhurst et al. | 548/543 |

FOREIGN PATENT DOCUMENTS

| 055215 | 6/1982 | European Pat. Off. |
| 129296 | 12/1984 | European Pat. Off. |
| 2612731 | 3/1976 | Fed. Rep. of Germany |

Primary Examiner—David B. Springer
Attorney, Agent, or Firm—Millen, White & Zelano

[57] ABSTRACT 1-(3-Substituted benzyl)-3-halogeno-4-(1-halogenoalkyl)-2-pyrrolidinones of the general formula (I):

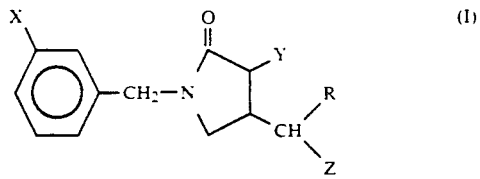

where X represents a hydrogen atom or halogen atom, Y and Z each represents a chlorine atom or bromine atom, and R represents an alkyl group with 2 to 4 carbon atoms, are herbicides useful in rice paddy fields to control weeds therein, especially Echinochloa crusgalli and can be produced subjecting the corresponding 3-dihalogeno compounds to dehalogenation to remove one of the halogen atoms or by cyclizing a 2,2-dihalogenoacetamide derivative represented by the general formula (II) under the presence of an appropriate catalyst:

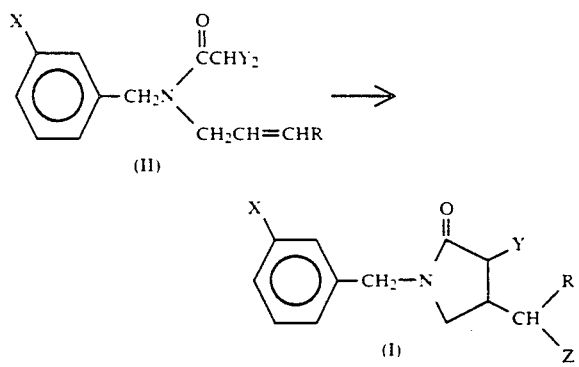

in which X, Y, Z and R respectively have the same meanings as described above.

15 Claims, No Drawings

1-(3-SUBSTITUTED BENZYL)-3-HALOGENO-4-(1-HALOGENO-ALKYL)-2-PYRROLIDINONE DERIVATIVES AND HERBICIDES CONTAINING THEM

BACKGROUND OF THE INVENTION

1. Field of the Invention

The present invention relates to novel 1-(3-substituted benzyl)-3-halogeno-4-(1-halogenoalky)-2-pyrrolidinone derivatives, to herbicides containing them and to processes for producing them.

2. Description of the Prior Art

It is disclosed that certain 2-pyrrolidinone derivatives have herbicidal activity in, for example, U.S. Pat. No. 4,110,105, U.S. Pat. No. 4,210,589 (division of U.S. Pat. No. 4,110,105), U.S. Pat. No. 4,069,038 (division of U.S. Pat. No. 4,119,636) or EP 134564A. Further, 3-chloro-4-chloromethyl-1-(3-trifluoromethylphenyl)-2-pyrrolidinone (common name, fluorochloridone), a typical compound disclosed in them, is already commercially available and has been put to practical use mainly for upland agriculture such as for winter wheat, cotton and sunflower. Further, physical properties and herbicidal test examples for two compounds, i.e., 1-benzyl-3-chloro-4-chloromethyl-2-pyrrolidinone and 1-(4-chlorobenzyl)-3-chloro-4-chloromethyl-2-pyrrolidinone are described in U.S. Pat. No. 4,110,105 and U.S. Pat. No. 4,210,589. In addition, U.S. Pat No. 4,132,713 discloses a process for producing pyrrolidinone derivatives of the following general formula and states that such derivatives are useful as a herbicide:

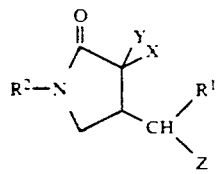

where X represents a hydrogen atom, chlorine atom or methyl group, Y represents a hydrogen atom, chlorine atom or bromine atom, Z represents a chlorine atom or bromine atom, $R^1$ represents a hydrogen atom or an alkyl group with 1 to 4 carbon atoms, $R^2$ represents an alkyl group with 1 to 6 carbon atoms, alkenyl group with 3 to 6 carbon atoms, a haloalkyl group with 1 to 6 carbon atoms, a cycloalkyl group with 3 to 6 carbon atoms, a cycloalkylalkyl group with 4 to 8 carbon atoms, benzyl group, chlorobenzyl group or represents the following formula:

where $R^3$ represents a hydrogen atom, alkyl group with 1 to 4 carbon atoms, acetyl group, chlorine atom, bromine atom, fluorine atom, iodine atom, trifluoromethyl group, nitro group, cyano group, alkoxy group with 1 to 4 carbon atoms, alkylthio group with 1 to 4 carbon atoms, alkylsulfinyl group with 1 to 4 carbon atoms, alkylsulfonyl group with 1 to 4 carbon atoms, trifluoromethylthio group, trifluoromethyl sulfinyl group, trifluoromethyl sulfonyl group, pentafluoropropione amide or 3-methyl ureido group and $R^4$ represents a hydrogen atom, alkyl group with 1 to 4 carbon atoms, chlorine atom or trifluoromethyl group.

When the compounds disclosed in U.S. Pat. Nos. 4,110,105 and 4,210,589, as well as in the examples of U.S. Pat. No. 4,132,713 are used as the herbicide, a relatively large dose is required. In particular, their herbicidal effect against Echinochloa crusgalli which is one of the most important weeds in the paddy field is extremely insufficient both in pre-emergence and post emergence treatments and causes severe phytotoxicity to the rice plant which is a useful crop.

OBJECT OF THE INVENTION

It is, accordingly, an object of the present invention to provide a selective herbicide giving no phytotoxicity to rice plant in the paddy field and having a herbicidal effect to harmful weeds mainly Echinochloa crusgalli at a low chemical dosage from the pre-emergence stage to the post-emergence growing stage. Other objects will be apparent to those skilled in the art to which this invention pertains.

The present inventors have made a further study on 2-pyrrolidinone derivatives for obtaining a herbicide that shows excellent herbicidal effect at a low dosage, gives no phytotoxicity to the rice plant and can be used over a long period of time from pre-emergence stage to the post-emergence growing stage of weeds, as compared with conventional paddy field herbicides. As a result, it has been found that a novel 1-(3-substituted benzyl)-3-halogeno-4-(1-halogenoalkyl)-2-pyrrolidinone derivative having a specific 1-chloroalkyl group or 1-bromoalkyl group at 4-position on the pyrrolidinone ring and having a benzyl group or a benzyl group substituted at 3-position with halogen at 1-position is excellent as a paddy field herbicide and gives no phytotoxicity to the rice plant as a useful crop.

SUMMARY OF THE INVENTION

The foregoing objects of the present invention can be attained by a 1-(3-substituted benzyl)-3-halogeno-4-(1-halogenoalkyl)-2-pyrrolidinone derivative of the general formula (I):

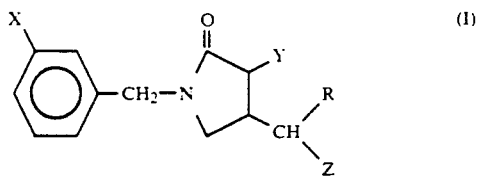

where X represents a hydrogen atom or halogen atom, Y and Z each represents a chlorine atom or bromine atom, and R represents a straight chain alkyl group with 2 to 4 carbon atoms, and a herbicide containing the above-mentioned compound as the effective ingredient.

DETAILED DESCRIPTION OF THE INVENTION

Illustrative of the compounds of this invention are those
 (a) in the form of the 3,4-cis isomer, substatially free from the 3,4-trans isomer;
 (b) wherein Y and Z both are Cl;
 (c) wherein X is H, Cl or F;
 (d) wherein R is $C_2H_5$ or $n-C_3H_7$; and (e) wherein Y and Z both are Cl, X is H, Cl or F and R is C$_2$H$_5$ or n-C$_3$H$_7$.

As used herein "propyl" and "C$_3$H$_7$" mean n-propyl.

The compounds according to the present invention have a structure similar to the prior art compounds described above, in which benzyl group or specific 3-halogen substituted benzyl group is present at 1-position on the pyrrolidinone group, and 1-chloroalkyl group or 1-bromoalkyl group with 3 to 5 carbon atoms is introduced into the 4-position. This transformation in structure produces an increase in the activity as an herbicide in the paddy field and an increase in the selectivity of their herbicidal activity between the rice plant and weeds. In addition, the effect against *Echinochloa frumentacea* in advanced leaf stages after emergence remains extremely high and they thus can be used over a longer period of time, viz., from pre-emergence stage to post-emergence stage of weeds.

Since the compounds disclosed in U.S. Pat. Nos. 4,110,105 and 4,210,589 require a relatively great amount of chemical dosage when actually used in flooded soils and, since they give a serious phytotoxicity to the rice plant, their use is extremely limited. The compound according to the present invention can be applied to paddy fields weeds at a lower dosage and applicable for a longer period of time from the pre-emergence stage to the post-emergence growing stage of weeds. In addition, no phytotoxicity to the rice plant is observed and they can be used with no hazard.

U.S. Pat. No. 4,132,713 discloses a process for producing an extremely wide range of compounds, including compounds otherwise corresponding to compounds of this invention but lacking one or more of a meta-halogen atom on the benzene ring, a bridging methylene group between the rings, and a halogenated alkyl group of 3-5 carbon atoms on the pyrrolidinon ring. However, actual preparation examples are described only for the preparation of the following compounds:

(1) 3-chloro-4-chloromethyl-1-(m-trifluoromethylphenyl)-2-pyrrolidinone (Examples 1-14)
(2) 3-chloro-4-chloromethyl-1-(2,6-diethylphenyl)-2-pyrrolidinone (Example 15)
(3) 4-chloromethyl-3,3-dichloro-1-(m-trifluoromethylphenyl)-2-pyrrolidinone (Example 16)
(4) 1-allyl-3-chloro-4-chloromethyl-2-pyrrolidinone (Example 17)
(5) 3-bromo-4-bromomethyl-1-(3-chlorophenyl)-2-pyrrolidinone (Example 18)

That is, the substituent on the 4-position of the pyrrolidinone ring is a halogenomethyl group in all of the cases.

Further, although it has been described that the compounds are useful as the hericide, the compounds shown in Examples 15, 16 and 18 of U.S. Pat. No. 4,132,713 exhibit only marginal herbicidal activity when used in the paddy field. Further, 3-chloro-4-chloromethyl-1-(m-trifluoromethylphenyl)-2-pyrrolidinone and 4-chloromethyl-3,3-dichloro-1-(m-trifluoromethylphenyl)-2-pyrrolidinone, when used in the paddy field, requires a relatively high dosage to be effective against *Echinochloa crusgalli*, an important weed, and is as phytotoxic or more so to the rice plant at that dosage, i.e., its selectivity is poor.

On the other hand, the compounds according to the present invention have a feature of introducing 1-chloroalkyl group or 1-bromoalkyl group with 3 to 5 carbon atoms to the 4-position of the pyrrolidinone group and, as a result, their improved herbicidal activity, they can be applied at a low dosage to the paddy field weeds and they can be applied over a longer period of time from the pre-emergence stage to the post-emergence growing stage of the weeds. In addition, no phytotoxicity to the rice plant is observed, so they can be used with greater safety. Further, the compounds according to the present invention have asymmetric carbon atoms at the 3-position and the 4-position of the pyrrolidinone ring and at the 1-position of the halogeno alkyl group substituted to the 4-position and thus may include four steric isomers (cis- and trans-isomers) due to asymmetric carbons at the 3-position and 4-position of the pyrrolidinone ring and corresponding diastereoisomers due to the asymmetric carbon atoms at the 4-position of the pyrrolidinone ring and the 1-position of the halogenoalky group substituted to the 4-position. The compounds according to the present invention have herbicidal activity in the form of a mixture of these isomers as it is but, in particular, a steric isomer thereof due to the asymmetric carbon atoms at the 3-position and the 4-position of the pyrrolidinone ring, that is, an isomer in which the halogen atom at the 3-position and the halogenoalky group at the 4-position are in a cis-form, is highly desirable in view of its herbicidal activity.

Herbicides containing a compound according to the present invention as a herbicidally effective ingredient exhibit an excellent herbicidal effect against most harmful weeds, for example, perennial broad leaf weeds or annual broad leaf weeds, for example, grassy weeds such as *Echinochloa crusgalli*, cyperaceou weeds such as *Cyperus microiria, Scirpus juncoides* and *Sagittaria pygmaea* and, in particular; they have a herbicidal activity at an extremely low chemical dosages from the pre-emergence stage to the post-emergence growing state of the weeds. On the other hand, the herbicides according to the compound of the present invention show no phytotoxicity to the rice plant, which is a useful crop, at dosages which are herbicidally effective against weeds.

The 1-(3-substituted benzyl)-3-halogeno-4-(1-halogenoalkyl)-2-pyrrolidinone derivatives represented by the general formula (I) according to the present invention are novel compound and can be prepared by subjecting a 2,2-dihalogenoacetamide derivative represented by the general formula (II) to a cyclizing reaction under the presence of an appropriate catalyst.

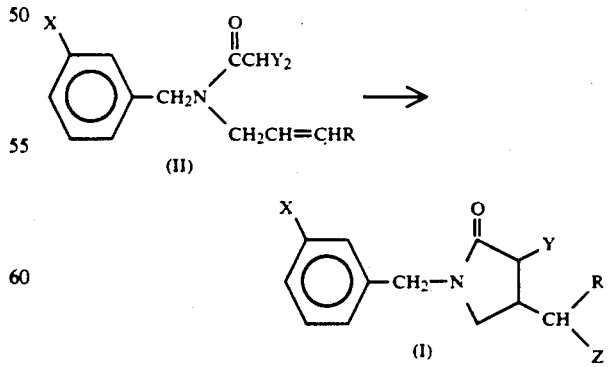

in which X, Y, Z and R respectively have the same meanings as described above.

The reaction is usually conducted in a solvent, preferably an inert solvent, i.e., one which does not hinder the reaction, for example, diethylene glycol dimethyl ether, dimethylsulfoxide, acetonitrile, dimethylformamide or an aromatic solvent such as benzene, toluene and xylene. As an appropriate catalyst, a transition metal catalyst, that is, one based on ferrous ions or cuprous ions, is preferred. As a specific transition metal catalyst, there can be mentioned ferrous chloride, cuprous chloride or cuprous bromide. In this case, a halogen atom derived from the metal catalyst can optionally be introduced at the 1-position of the alkyl group (represented by Z) at the 4-position of the pyrrolidinone group of a compound of the general formula (I). Specifically, those compounds in which Y represents a chlorine atom, Z represents a bromine atom or Y represents a bromine atom and Z represents a chlorine atom can be synthesized.

For promoting the reaction, it is also effective to add amines in the reaction mixture. The reaction temperature is from 20° to 190° C., preferably, from 70° to 140° C.

1-(3-substituted benzyl)-3-halogeno-4-(1-halogenoalkyl)-2-pyrrolidinone derivative obtained by the process of the present invention is a mixture of four steric isomers described above.

The amide derivative represented by the general formula (II) can be produced by reacting an amine of the general formula (III) and a carboxylic acid derivative of the general formula (IV):

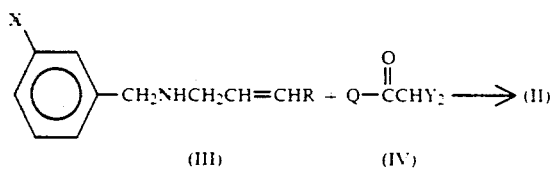

where X, Y and R have the same meanings as described above and Q represents halogen.

The reaction is conducted without solvent or in an inert solvent. As the inert solvent, there can be mentioned, for example, aromatic hydrocarbons such as benzene, toluene, xylene, chlorobenzene, dichlorobenzene and cumene, halogenated hydrocarbons such as dichloromethane, chloroform and carbon tetrachloride, ethers such as diethyl ether, tetrahydrofuran and dioxane and ester such as ethyl acetate and butyl acetate. The reaction can be proceeded at a optional temperature and the reaction may be conducted under the presence of an organic or inorganic base such as triethylamine, pyridine, sodium hydride, potassium hydride, sodium carbonate, potassium carbonate and potassium hydrogen carbonate.

The amines of the ge neral formula (III) are prepared by a method, for example, of reacting a benzylamine derivative and a halogenated alkyl derivative, preferably, in a solvent such as dimethylformamide.

Alternatively, the compound according to the present invention can also be prepared by the method as described below. According to this method, four steric isomers due to asymmetric carbon atoms at the 3-position and 4-position of the pyrrolidinone group and at the 1-position of the 1-halogenoalkyl group substituted to the 4-position thereof can be separated easily.

That is, 3,3-dihalogenopyrrolidinone derivative represented by the formula (VI) is obtained by the cyclizing reaction of a 2,2,2-trihalogeno acetamide derivative of the general formula (V):

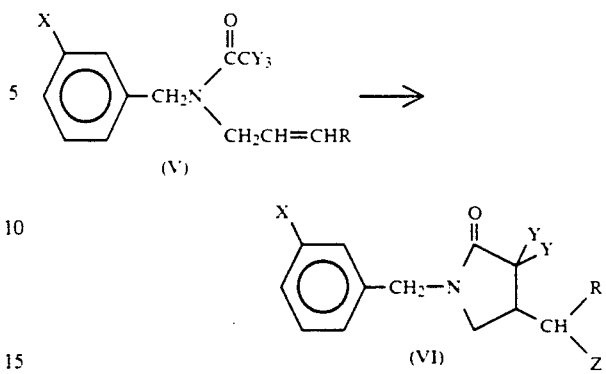

where X, Y, Z and R have the same meanings as described above.

The reaction is generally conducted in a solvent, preferably, a solvent not hindering the reaction, that is, dimethylene glycol dimethyl ether, dimethylformamide, dimethyl sulfoxide, acetonitrile or aromatic hydrocarbon solvent such as benzene, toluene or xylene. As a suitable catalyst, transition metal catalysts, that is, ferrous ions or cuprous ions are preferred. As a specific transition metal catalyst, there can be mentioned ferrous chloride, cuprous chloride or cuprous bromide. In this case, by using an excess amount of the catalyst such as cuprous chloride or cuprous bromide, preferably, by two or greater molar amount, optional halogen atom derived from the metal catalyst can be introduced to the 1-position of the alkyl group (represented by Z) at the 4-position on the pyrrolidinone group represented by the general formula (VI). Specifically, a compound in which Y represents a chlorine atom, Z represents a bromine atom or Y represents a bromine and Z represents a chlorine atom can be synthesized. Further, for accelerating the reaction, it is extremely effective to add various amines such as di-normal butylamine into the reaction solution.

The reaction temperature is from 20° to 190° C., preferably, from 60° to 140° C.

3,3-dihalogenopyrrolidinone derivative of the general formula (VI) obtained by reaction is a mixture of diastereoisomers produced by the asymmetric carbon atoms at the 4-position of the pyrrolidinone group and at the 1-position of the 1-halogenoalkyl group introduced to the 4-position and the mixture can easily be separated by general separation means, for example, recrystallization or column chromatography.

The aimed compound according to the present invention of the general formula(I) can be obtained by subjecting the thus obtained respective 3,3-dihalogenopyrrolidinone derivatives of the general formula (VI) to a dehalogenating reaction in accordance with the following process:

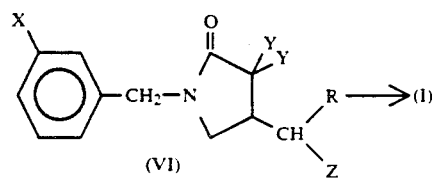

where X, Y, Z and R have the same meanings as described above.

The reaction is conducted without solvent or in a solvent under the presence of an appropriate reducing agent. As the reducing agent, there can be mentioned metal such as iron, zinc, tin and copper or an organic tin compound such as dibutyltin hydride, tributyltin hydride, dipheyltin hydride and triphenyltin hydride. Further, hydrogenation can be conducted by using palladium carbon, Raney nickel or platinum and, depending on the case, electrolytic reduction may also be employed. As an appropriate solvent, there can be mentioned aromatic hydrocarbons such as benzene, toluene and xylene, ethers such as diethyl ether, tetrahydrofuran and dioxane, esters such as ethyl acetate, butyl acetate, lower alcohols such as methanol, ethanol, propanol and butanol and lower organic acid such as acetic acid, propionic acid and lactic acid. The reaction temperature is from −30° to 100° C. and reaction may be conducted at a refluxing temperature of the solvent. The reaction time is within 50 hours and the reaction may be conducted under the presence of an appropriate organic acid such as acetic acid or formic acid or an alkali metal salt thereof, or an appropriate mineral acid such as hydrochloric acid.

1-(3-substituted benzyl)-3-halogeno-4-(1-halogenoalkyl)-2-pyrrolidinone derivative of the general formula (I) obtained by this reaction is a mixture of steric isomers produced due to the asymmetric carbon atoms at the 3-position and 4-position of the pyrrolidinone group and can easily be separated and purified by various separation means such as recrystallization and column chromatography.

A trihalogenoacetamide derivative represented by the general formula (V) can be prepared by reacting an amine of the general formula (III) and a carboxylic acid derivative of the general formula (VII):

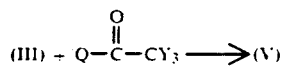

where X, Y and R have the same meaning as described above and Q represents halogen.

The reaction is conducted without solvent or in an inert solvent. As the inert solvent, there can be mentioned, for example, aromatic hydrocarbons such as benzene, toluene, xylene, chlorobenzene, dichlorobenzene and cumene, halogenated hydrocarbons such as dichloromethane, chloroform and carbon tetrachloride, ethers such as diethyl ether, tetrahydrofuran and dioxane and esters such as ethyl acetate and butyl acetate. The reaction can be proceeded at a optional temperature and the reaction may be conducted under the presence of an organic or inorganic base such as triethylamine, pyridine, sodium hydride, potassium hydride, sodium carbonate, potassium carbonate and potassium hydrogen carbonate.

The compound represented by the general formula (I) according to the present invention thus obtained is usually mixed with an inert liquid or solid carrier and used after being prepared into the form of formulation usually employed, for example, dust, granule, wettable powder, emulsifiable concentrate, flowable formulation, etc. Further, adjuvants may also be added if required in view of formulation.

As a carrier, either solid or liquid carrier may be used so long as it is usually used for agricultural and horticultural chemicals, with no restriction to particular materials.

As the solid carrier, there can be mentioned, for example, mineral powder such as clay, talc, bentonite, calcium carbonate, diatomaceous earth or white carbon, vegetable powder such as soybean powder or starch, polymeric compound such as petroleum resin, polyvinyl alcohol or polyalkylene glycol, urea, wax, etc. Further, as the liquid carrier, there can be mentioned, for example, various kinds of organic solvents and water.

As the adjuvant, surface active agent, binder, stabilizer, etc. usually employed for agricultural and horticultural chemicals may be used alone or in combination as required. Furthermore, industrial bacteriocide of antibacteria or antifungus agent may also be added with an aim of controlling bacteria and fungi.

As an example of the surface active agent, nonionic, anionic, cationic and amphoteric agents may be used properly alone or in admixture. As the nonionic surface active agents, those prepared by adding ethylene oxide or propylene oxide to alkylphenyl, higher alcohol, alkyl naphthol, higher fatty acid or fatty acid ester are preferred. As the anionic agent, alkyl sulfonate, alkyl sulfate ester, phosphate ester from alkyl phenol, alkyl naphthol, higher alcohol, higher fatty acid or fatty acid ester are preferred. Further, a lignin sulfonate is one of preferred examples.

The content of the compound represented by the general formula (I) in the herbicide according to the present invention, while varying depending on the formulations, is usually from 0.05 to 20% by weight for the dust, from 1 to 50% by weight for the wettable powder, from 0.05 to 15% by weight for the granule, from 1 to 50% by weight for the emulsifiable concentrate, from 4 to 50% by weight for the flowable formulation and from 1 to 50% by weight for the dry flowable formulation. Preferably, it is from 0.5 to 5% by weight for the dust, from 10 to 40% by weight for the wettable powder, from 0.5 to 8% by weight for the granule, from 10 to 20% by weight for the emulsifiable concentrate, from 20 to 30% by weight for the flowable formulation and from 20 to 40% by weight for the dry flowable formulation.

The application amount is generally, from 3 to 300 g per 10 are as the effective ingredient.

The herbicide according to the present invention can be used in admixture with other herbicides, insecticides, plant growth controlling agent, fertilizer or soil improver and, depending on the case, a synergistic effect can also be expected.

EXAMPLE

The process for synthesizing the compound according to the present invention is to be described in more details referring to examples.

EXAMPLE 1

Synthesis of
1-(3-chlorobenzyl)-3-chloro-4-(1-chloropropyl)-2-pyrrolidinone (Compound No. 1)

N-(3-chlorobenzyl)-N-(2-pentenyl)-2,2-dichloroacetamide was added by 1 g into 15 ml of xylene, to which 2 g of di-normal-butylamine and 0.5 g of cuprous chloride were added under stirring at 90° C. After continuing stirring for one hour, 40 ml of 20% hydrochloric acid was added and extracted with toluene. The extract was dried with anhydrous magnesium sulfate, concentrated by an evaporator and then purified on silica gel chromatography (hexane/ethyl acetate=3/1, v/v) to obtain 0.6 g of an oily product. This was a mixture of four isomers.

EXAMPLE 2

Synthesis of 1-benzyl-3,3-dichloro-4-(1-chlorobutyl)-2-pyrrolidinone (Compound Nos. i and ii)

N-benzyl-N-(2-hexenyl)-2,2,2-trichloroacetamide was added by 20 g into 200 ml of toluene, to which 4 ml of di-normal-butylamine and 3.6 g of cuprous chloride were added under stirring at 90° C. After continuing stirring for one hour, 200 ml of 20% hydrochloric acid was added and extracted with toluene. The extract was dried with anhydrous magnesium sulfate, concentrated by an evaporator and then purified on silica gel chromatography (hexane/ethyl acetate=6/1, v/v) to obtain 13 g of an initially eluted compound (Compound No. i) and 2 g of a subsequently eluted compound (Compound No. ii). The compounds of the Compound Nos. i and ii are diasteromers due to asymmetric carbon atoms at the 4-position on the pyrrolidinone ring and at the 1-position of the halogenoalkyl group substituted to the 4-position.

EXAMPLE 3

Synthesis of 1-benzyl-4-(1-chlorobutyl)-3-chloro-2-pyrrolidinone (Compound Nos. 2, 3)

The compound eluted initially obtained in Example 2 (Compound No. i) was dissolved by 1 g into 20 ml of ethyl acetate, to which 0.5 g of sodium acetate and 0.22 g of 5%-palladium carbon were added and hydrogenated at a normal temperature and a normal pressure. After three hours, carbon was removed by filtration. 30 ml of water was added and extracted with ethyl acetate. After drying with anhydrous sodium sulfate, the residue was concentrated by an evaporator and then subjected to silica gel column chromatography (hexane/dichloromethane/ethyl acetate=7/2/1, v/v/v) to obtain 0.2 g of an initially eluted compound (Compound No. 2) and 0.4 g of a compound eluted subsequently (Compound No. 3). The compounds of Compound Nos. 2 and 3 are steric isomers due to the asymmetric carbon atoms at the 3-position and the 4-position of the pyrrolidinone ring.

EXAMPLE 4

Synthesis of 1-benzyl-3-chloro-4-(1-chlorobutyl)-2-pyrrolidinone (Compound Nos. 4, 5)

The subsequently eluted compound obtained in Example 2 (Compound No. ii) was dissolved by 1 g into 10 ml of tetrahydrofuran, to which 0.2 g of zinc powder was added and, while stirring at 0° C., 0.4 g of acetic acid was added. Then, stirring was conducted at it was for 30 min and 40 ml of water was added and extracted with ethyl acetate. After drying the extract with anhydrous sodium sulfate, the residue was concentrated in an evaporated and subjected to silica gel column chromatography (hexane/ethyl acetate=4/1, v/v), to obtain 0.44 g of an initially eluted compound (Compound No. 4) and 0.28 g of a compound eluted subsequently (Compound No. 5). The compounds of Compound Nos. 4 and 5 were steric isomers due to the asymmetic carbon atoms at the 3-position and the 4-position of the pyrrolidinone ring.

EXAMPLE 5

Synthesis of 1-benzyl-4-(1-bromobutyl)-3,3-dichloro-2-pyrrolidinone (Compound No. xxii)

2.5 g of cuprous bromide and 2.3 g of di-normal-butylamine were added to 20 ml of toluene and heated to 70° C. while stirring. 2.0 g of N-benzyl-N-(2-hexenyl)-2,2,2-trichloroacetamide dissolved in 10 ml of toluene was dropped and stirred at a temperature lower than 80° C. for 12 min. It was concentrated in an evaporator and subjected to silica gel column chromatography (hexane/ethyl acetate=9/1, v/v) to obtain 0.78 g of the initially eluted compound (Compound No. xxii).

In accordance with the procedures of example 2 or Example 5, various 3,3-dihalogeno-2-pyrrolidinone derivatives of the general formula (VI) as the important intermediate products were synthesized. The compounds and their physical properties are shown together with Compound Nos. in Table 1.

Further, the compounds according to the present invention represented by the general formula (I) were synthesized from 3,3-dihalogeno-2-pyrrolidinone derivatives of the general formula (VI) stated in Table 1 in accordance with the procedures in Example 3 or Example 4. The compounds and physical properties are shown together with the Compound Nos. in Table 2. In Table 2, Compound No. 3 and Compound No. 5, for example, are diastereoisomers due to the asymetric carbon atoms at the 4-position of the pyrrolidinone ring and the 1-position of the halogenoalkyl group substituted to the 4-position. The Compound Nos. are referred to hereinafter, for example, also to preparation examples and herbicidal test examples.

TABLE 1

(VI)

| Compound No. | Substituents in formula (IV) X | Y | Z | R | Physical properties |
|---|---|---|---|---|---|
| i | H | Cl | Cl | C₃H₇ | IR(nujol): 1720cm⁻¹, NMR(CDCl₃)δ: 1.01(3H, t, J=7.3Hz), 1.40–1.90(3H, m), 2.21–2.33(1H, m), 2.97–3.12(2H, m), 3.49(1H, dd, J=9.9Hz, 6.9Hz), 4.20–4.28(1H, m), 4.43(1H, d, J=14.9Hz), 4.64(1H, d, J=14.9Hz), 7.14–7.26(2H, m), 7.28–7.40(3H, m), m.p.: 71.0–72.0° C. |
| ii | H | Cl | Cl | C₃H₇ | IR(film): 1720cm⁻¹, NMR(CDCl₃)δ: 0.90(3H, t, J=7.3Hz), 1.38–1.71(4H, m), 3.00–3.13(2H, m), 3.27–3.40(1H, m), 4.20–4.27(1H, m), 4.42(1H, d, J=14.9Hz), 4.63(1H, d, J=14.9Hz), 7.20–7.29(2H, m), 7.30–7.40(3H, m). |
| iii | Cl | Cl | Cl | C₃H₇ | IR(film): 1720cm⁻¹, NMR(CDCl₃)δ: 0.99(3H, t, J=7.3Hz), 1.43–1.91(3H, m), 2.21–2.32(1H, m), 2.96–3.14(2H, m), 3.28–3.40(1H, m), 4.22–4.30(1H, m), 3.50(1H, dd, J=9.9Hz, 6.6Hz), 4.21–4.30(1H, m), 4.40(1H, d, J=14.9Hz), 4.61(1H, d, J=14.9Hz), 7.10–7.15(1H, m), 7.24–7.38(3H, m). |
| iv | Cl | Cl | Cl | C₃H₇ | IR(film): 1720cm⁻¹, NMR(CDCl₃)δ: 0.91(3H, t, J=7.6Hz), 1.35–1.73(4H, m), 3.02–3.16(2H, m), 3.28–3.38(1H, m), 4.22–4.30(1H, m), 4.40(1H, d, J=14.9Hz), 4.61(1H, d, J=14.9Hz), 7.13–7.19(1H, m), 7.21–7.41(3H, m). |
| v | Br | Cl | Cl | C₃H₇ | IR(film): 1720cm⁻¹, NMR(CDCl₃)δ: 0.99(3H, t, J=7.3Hz), 1.40–1.90(3H, m), 2.21–2.32(1H, m), 2.95–3.15(2H, m), 3.49(1H, dd, J=9.9Hz, 6.6Hz), 4.21–4.30(1H, m), 4.63(1H, d, J=14.6Hz), 7.18(1H, d, J=6.0Hz), 7.25(1H, t, J=6.0Hz), 7.50(1H, s), 7.58(1H, d, J=6.0Hz) |
| vi | Br | Cl | Cl | C₃H₇ | IR(film): 1720cm⁻¹, NMR(CDCl₃)δ: 0.91(3H, t, J=7.6Hz), 1.35–1.73(4H, m), 2.98–3.15(2H, m), 3.28–3.36(1H, m), 4.22–4.30(1H, m), 4.42(1H, d, J=14.9Hz), 4.66(1H, d, J=14.9Hz), 7.18(1H, d, J=6.0Hz), 7.40(1H, s), 7.48(1H, d, J=6.0Hz) |
| vii | F | Cl | Cl | C₃H₇ | IR(nujol): 1720cm⁻¹, NMR(CDCl₃)δ: 0.99(3H, t, J=7.3Hz), 1.45–1.91(3H, m), 2.21–2.33(1H, m), 2.96–3.14(2H, m), 3.50(1H, dd, J=10.0Hz, 6.9Hz), 4.21–4.29(1H, m), 4.45(1H, d, J=14.9Hz), 4.64(1H, d, J=14.9Hz), 6.93–7.08(3H, m), 7.26–7.38(1H, m), m.p.: 65.0–68.0° C. |
| viii | F | Cl | Cl | C₃H₇ | IR(film): 1720cm⁻¹, NMR(CDCl₃)δ: 0.84–0.96(3H, m), 1.25–1.70(4H, m), 3.03–3.14(2H, m), 3.30–3.39(1H, m), 4.21–4.28(1H, m), 4.41(1H, d, J=14.9Hz), 4.62(1H, d, J=14.9Hz), 6.94–7.05(3H, m), 7.28–7.38(1H, m). |
| ix | H | Cl | Cl | C₂H₅ | IR(film): 1720cm⁻¹, NMR(CDCl₃)δ: 1.13(3H, t, J=7.6Hz), 1.75–1.95(1H, m), 2.28–2.44(1H, m), 2.93–3.13(2H, m), 3.48(1H, dd, J=9.6Hz, 6.6Hz), 4.15–4.23(1H, m), 4.44(1H, d, J=14.8Hz), 4.63(1H, d, J=14.8Hz), 7.23–7.26(2H, m), 7.31–7.42(3H, m). |
| x | H | Cl | Cl | C₂H₅ | IR(film): 1720cm⁻¹, NMR(CDCl₃)δ: 1.06(3H, t, J=7.6Hz), 1.40–1.77(2H, m), 2.97–3.12(2H, m), 3.29(1H, dd, J=8.9Hz, 6.5Hz), 7.31–7.42(3H, m), 4.14–4.22(1H, m), 4.44(1H, d, J=14.9Hz), 4.62(1H, d, J=14.9Hz), 7.23–7.28(2H, m), 7.31–7.42(3H, m). |
| xi | Cl | Cl | Cl | C₂H₅ | IR(film): 1720cm⁻¹, NMR(CDCl₃)δ1.14(3H, t, J=7.6Hz), 1.80–1.96(1H, m), 2.23–2.43(1H, m), 2.97–3.14(2H, m), 3.49(1H, dd, J=10.0Hz, 6.9Hz), 4.17–4.25(1H, m), 4.40(1H, d, J=14.9Hz), 7.07–7.16(1H, m), 7.24–7.34(3H, m) |
| xii | Cl | Cl | Cl | C₂H₅ | IR(film): 1720cm⁻¹, NMR(CDCl₃)δ: 1.08(3H, t, J=7.6Hz), 1.40–1.58(1H, m), 1.66–1.79(1H, m), 2.96–3.14(2H, m), 3.32(1H, dd, J=8.9Hz, 6.5Hz), 4.14–4.23(1H, m), 4.40(1H, d, J=14.9Hz), 4.66(1H, d, J=14.9Hz), 7.12–7.15(1H, m), 7.20–7.38(3H, m) |
| xiii | Br | Cl | Cl | C₂H₅ | IR(film): 1720cm⁻¹, nD 24.3° C.: 1.5015 |
| xiv | Br | Cl | Cl | C₂H₅ | IR(film): 1720cm⁻¹, nD 24.2° C.: 1.5048 |
| xv | F | Cl | Cl | C₂H₅ | IR(film): 1720cm⁻¹, nD 22.3° C.: 1.5374 |
| xvi | F | Cl | Cl | C₂H₅ | IR(KBr): 1720cm⁻¹, m.p. 100.3–101.8° C. |
| xvii | H | Cl | Cl | C₄H₉ | IR(film): 1720cm⁻¹, NMR(CDCl₃)δ:0.94 (3H, t, J=7.3Hz), 1.23–1.72(4H, m), 1.76–1.99(1H, m), 2.25–2.38(1H, m), 2.94–3.14(2H, m), 3.48(1H, dd, J=9.9Hz, 6.6Hz), 4.18–4.28(1H, m), 4.44(1H, d, J=14.9Hz), 4.63(1H, d, J=14.9Hz), 7.22–7.27(2H, m), 7.31–7.42(3H, m) |
| xviii | H | Cl | Cl | C₄H₉ | IR(film): 1720cm⁻¹, NMR(CDCl₃)δ: 0.89(3H, t, J=7.3Hz), 1.14–1.60(6H, m), 3.00–3.12(2H, m), 3.26–3.34(1H, m), 4.20–4.27(1H, m), 4.43(3H, t, J=14.9Hz), 4.63(1H, d, J=14.9Hz), 7.22–7.29(2H, m), 7.31–7.44(3H, m) |
| xix | Cl | Cl | Cl | C₄H₉ | IR(film): 1720cm⁻¹, NMR(CDCl₃)δ: 0.95(3H, t, J=7.3Hz), 1.23–1.72(4H, m), 1.77–1.99(1H, m), 2.23–2.37(1H, m), 2.97–3.14(2H, m), 3.49(1H, dd, J=9.7Hz, 6.6Hz), 4.20–4.29(1H, m), 4.55(1H, d, J=14.9Hz), 4.61(1H, d, J=14.9Hz), 7.11–7.17(1H, m), 7.24–7.34(3H, m) |
| xx | Cl | Cl | Cl | C₄H₉ | IR(film): 1720cm⁻¹, NMR(CDCl₃)δ: 0.90(3H, t, J=7.6Hz), 1.22–1.62(6H, m), 3.01–3.14(2H, m), 3.33(1H, m), 4.22–4.27(1H, m), 4.40(1H, d, J=14.9Hz), 4.61(1H, d, J=14.9Hz), 7.13–7.16(1H, m), 7.22–7.33(3H, m) |
| xxi | H | Br | Br | C₃H₇ | IR(KBr): 1710, 1420, 1270, 1250cm⁻¹, m.p.: 88.5–90.0° C. |
| xxii | H | Cl | Br | C₃H₇ | IR(KBr): 1710cm⁻¹ m.p.: 93.5–96.0° C. Elemental Analysis(observed): C 47.42; H 4.80; Cl 18.26; Br 20.97; N 3.58; Calculated as C₁₅H₁₈BrCl₂NO: C 47.52; H 4.78; Br 21.08; Cl 18.70; N 3.69%) |

TABLE 2

(I)

[Structure: A pyrrolidinone ring with N-CH2-phenyl group (phenyl bearing X and Y substituents), C=O at position 2, Y substituent at position 3, and CH(R)-Z at position 4]

| Compound No. | Substituents of formula (I) | | | | | Geometric isomerism | Physical properties | Source No. |
|---|---|---|---|---|---|---|---|---|
| | X | Y | Z | R | | | | |
| 1 | Cl | Cl | Cl | C2H5 | | Mixture of 3,4-cis and 3,4-trans | IR(film): 1700cm⁻¹, nD 23.4° C.: 1.5475 | i |
| 2 | Cl | H | Cl | C3H7 | | 3,4-trans | IR(film): 1700cm⁻¹, ¹NMR(CDCl3)δ: 0.93(3H, t, J = 7.6Hz), 1.34–1.76(4H, m), 2.73(1H, m), 3.28(2H, m), 4.20(1H, m), 4.40(1H, d, J = 14.9Hz)4.55(1H, d, J = 8.9Hz), 4.60(1H, d, J = 14.9Hz), 7.23(2H, m), 7.34(3H, m) | i |
| 3 | H | Cl | Cl | C3H7 | | 3,4-cis | IR(KBr): 1690, 1470cm⁻¹, ¹NMR(CDCl3)δ: 0.96(3H, t, J = 9.5Hz), 1.35–1.70(3H, m), 1.85(1H, m), 2.70(1H, m), 3.25(1H, t, J = 9.5Hz), 4.45(1H, dd, J = 9.5Hz), 4.10(1H, m), 4.35(1H, d, J = 5.9Hz), 4.40(1H, d, J = 14.9Hz), 4.60(1H, d, J = 14.9Hz), 7.22(2H, m), 7.33(3H, m) m.p. = 90.2–91.2° C. | ii |
| 4 | H | Cl | Cl | C3H7 | | 3,4-trans | IR(film): 1700cm⁻¹, ¹NMR(CDCl3)δ: 0.93(3H, t, J = 7.6Hz), 1.35–1.70(2H, m), 1.73–1.90(2H, m), 2.87(1H, m), 3.22(1H, dd, J = 10.0Hz, 5.9Hz), 3.40(1H, t, J = 10.0Hz), 3.97(1H, m), 4.41(1H, d, J = 14.9Hz), 4.59(1H, d, J = 14.9Hz), 4.62(1H, d, J = 6.5Hz), 7.23(2H, m), 7.34(3H, m) | ii |
| 5 | H | Cl | Cl | C3H7 | | 3,4-cis | IR(film): 1700cm⁻¹, ¹NMR(CDCl3)δ: 0.91(3H, t, J = 7.0Hz), 1.35–1.70(4H, m), 2.87(1H, m), 3.10(1H, t, J = 9.5Hz), 3.19(1H, dd, J = 9.5Hz, 7.3Hz), 4.10(1H, m), 4.36(1H, m), 4.55(1H, d, J = 14.3Hz), 4.10(1H, m), 4.63(1H, d, J = 14.3Hz), 7.23(2H, m), 7.34(3H, m) | iii |
| 6 | Cl | Cl | Cl | C3H7 | | 3,4-trans | IR(film): 1700cm⁻¹, ¹NMR(CDCl3)δ: 0.94(3H, t, J = 7.6Hz), 1.34–1.76(4H, m), 2.71–2.81(1H, m), 3.31–3.46(2H, m), 4.17–4.25(1H, m), 4.38(1H, d, J = 14.9Hz), 4.54(1H, d, J = 8.4Hz), 4.58(1H, d, J = 14.9Hz), 7.12–7.19(1H, m), 7.24–7.36(3H, m) | iii |
| 7 | Cl | Cl | Cl | C3H7 | | 3,4-cis | IR(film): 1700cm⁻¹, ¹NMR(CDCl3)δ: 0.96(3H, t, J = 7.6Hz), 1.40–1.75(3H, m), 1.80–1.93(1H, m), 2.63–2.78(1H, m), 3.27(1H, t, J = 10.0Hz), 3.46(1H, m), 4.07–4.16(1H, m), 4.36(1H, d, J = 6.5Hz), 4.38(1H, d, J = 14.9Hz), 4.56(1H, m), 7.12–7.15(1H, m), 7.24–7.37(3H, m) | iv |
| 8 | Cl | Cl | Cl | C3H7 | | 3,4-trans | IR(film): 1700cm⁻¹, ¹NMR(CDCl3)δ: 0.94(3H, t, J = 7.6Hz), 1.38–1.70(2H, m), 1.73–1.95(2H, m), 2.85–2.94(1H, m), 3.24(1H, dd, J = 10.0Hz, 5.9Hz), 3.43(1H, t, J = 10.0Hz), 3.96–4.03(1H, m), 4.41(1H, d, J = 14.9Hz), 4.55(1H, d, J = 6.5Hz), 4.62(1H, d, J = 14.9Hz), 7.12–7.17(1H, m), 7.20–7.37(3H, m) | iv |
| 9 | Cl | Cl | Cl | C3H7 | | 3,4-cis | IR(film): 1700cm⁻¹, ¹NMR(CDCl3)δ: 0.93(3H, t, J = 7.0Hz), 1.37–1.71(4H, m), 2.70–2.82(1H, m), 3.07–3.23(2H, m), 4.08–4.16(1H, m), 4.33(1H, d, J = 14.9Hz), 4.56(1H, d, J = 5.4Hz), 4.59(1H, d, J = 14.9Hz), 7.10–7.18(1H, m), 7.22–7.30(3H, m) | v |
| 10 | Br | Cl | Cl | C3H7 | | 3,4-trans | IR(film): 1700cm⁻¹, nD 21.5° C.: 1.4802 | v |
| 11 | Br | Cl | Cl | C3H7 | | 3,4-cis | IR(film): 1700cm⁻¹, nD 21.6° C.: 1.5336 | vi |
| 12 | Br | Cl | Cl | C3H7 | | 3,4-trans | IR(film): 1700cm⁻¹, nD 20.4° C.: 1.5343 | vi |
| 13 | Br | Cl | Cl | C3H7 | | 3,4-cis | IR(film): 1700cm⁻¹, nD 20.5° C.: 1.5580 | vii |
| 14 | F | Cl | Cl | C3H7 | | 3,4-trans | IR(film): 1700cm⁻¹, ¹NMR(CDCl3)δ: 0.93(3H, t, J = 7.0Hz), 1.34–1.70(4H, m), 2.71–2.82(1H, m), 3.23–3.38(2H, m), 4.17–4.24(1H, m), 4.42(1H, d, J = 14.9Hz), 4.54(1H, d, J = 8.4Hz), 4.63(1H, d, J = 14.9Hz), 6.94–7.04(3H, m), 7.28–7.36(1H, m) | vii |
| 15 | F | Cl | Cl | C3H7 | | 3,4-cis | IR(film): 1700cm⁻¹, ¹NMR(CDCl3)δ: 0.94(3H, t, J = 7.6Hz), 1.30–1.72(3H, m), 1.82–1.93(1H, m), 2.63–2.80(1H, m), 3.23(1H, dd, J = 10.0Hz, 7.3Hz), 3.46(1H, dd, J = 10.0Hz, 7.3Hz), 4.08–4.17(1H, m), 4.36(1H, d, J = 5.9Hz), 4.39(1H, d, J = 14.9Hz), 4.60(1H, d, J = 14.9Hz), 6.94–7.04(3H, m), 7.27–7.37(1H, m) | viii |
| 16 | F | Cl | Cl | C3H7 | | 3,4-trans | IR(film): 1700cm⁻¹, nD 22.5° C.: 1.5162 | viii |
| 17 | F | Cl | Cl | C3H7 | | 3,4-cis | IR(film): 1700cm⁻¹, nD 22.5° C.: 1.5177 | ix |
| 18 | H | Cl | Cl | C2H5 | | 3,4-trans | IR(film): 1700cm⁻¹, ¹NMR(CDCl3)δ: 1.07(3H, t, J = 7.4Hz), 1.65–1.88(2H, m), 2.71–2.83(1H, m), 3.25–3.34(2H, m), 4.05–4.15(1H, m), 4.42(1H, d, J = 14.9Hz), 4.54(1H, d, J = 8.8Hz), 4.62(1H, d, J = 14.9Hz), 7.22–7.26(2H, m), 7.29–7.40(3H, m) | |

TABLE 2-continued

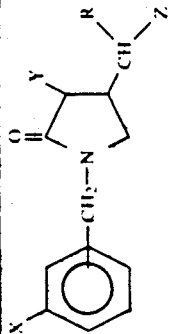

(I)

| Compound No. | Substituents of formula (I) | | | | Geometric isomerism | Physical properties | Source No. |
|---|---|---|---|---|---|---|---|
| | X | Y | Z | R | | | |
| 19 | H | Cl | Cl | C₂H₅ | 3,4-cis | IR(film)1700cm⁻¹, NMR(CDCl₃)δ: 1.07(3H, t, J = 7.3Hz), 1.60 – 1.84(2H, m), 2.70 – 2.85(1H, m), 3.28(1H, t, J 10.5Hz, 7.0Hz), 4.02 – 4.12(1H, m), 4.34(1H, d, J 6.0Hz), 4.40(1H, d, J = 14.9Hz), 4.64(1H, dd, J = 14.9Hz), 7.23 – 7.28(2H, m), 7.31 – 7.39(3H, m) | ix |
| 20 | H | Cl | Cl | C₂H₅ | 3,4-trans | IR(film): 1700cm⁻¹, NMR(CDCl₃)δ: 1.07(3H, t, J = 7.3Hz), 1.82 – 1.94(2H, m), 2.83 – 2.92(1H, m), 3.21(1H, dd, J 10.0Hz, 6.5Hz), 3.38(1H, t, J 10.0Hz), 3.83 – 3.92(1H, m), 4.41(1H, d, J = 14.9Hz), 4.60(1H, d, J = 14.9Hz), 4.63(1H, d, J = 6.2Hz), 7.23 – 7.26(2H, m), 7.30 – 7.39(3H, m) | x |
| 21 | H | Cl | Cl | C₂H₅ | 3,4-cis | IR(film): 1700cm⁻¹, NMR(CDCl₃)δ: 1.03(3H, t, J = 7.4Hz), 1.45 – 1.78(2H, m), 2.70 – 2.83(1H, m), 3.05 – 3.22(1H, m), 4.02 – 4.13(1H, m), 4.35(1H, d, J 5.7Hz), 4.55(1H, d, J = 14.9Hz), 4.62(1H, d, J = 14.9Hz), 7.21 – 7.26(2H, m), 7.31 – 7.39(3H, m) | x |
| 22 | Cl | Cl | Cl | C₂H₅ | 3,4-trans | IR(film): 1700cm⁻¹, NMR(CDCl₃)δ: 1.09(3H, t, J = 7.4Hz), 1.65 – 1.85(2H, m), 2.72 – 2.85(1H, m), 3.23 – 3.33(2H, m), 4.07 – 4.15(1H, m), 4.38(1H, d, J = 14.9Hz), 4.53(1H, d, J 8.9Hz), 4.57(1H, d, J = 14.9Hz), 7.10 – 7.17(1H, m), 7.22 – 7.31(3H, m) | xi |
| 23 | Cl | Cl | Cl | C₂H₅ | 3,4-cis | IR(film): 1700cm⁻¹, NMR(CDCl₃)δ: 1.10(3H, t, J = 7.3Hz), 1.73 – 1.87(1H, m), 1.93 – 2.06(1H, m), 2.67 – 2.82(1H, m), 3.30(1H, t, J = 10.5Hz), 3.45(1H, dd, J = 14.9Hz, 6.9Hz), 4.02 – 4.11(1H, m), 4.36(1H, d, J 6.0Hz), 4.39(1H, d, J = 14.9Hz), 4.58(1H, d, J = 14.9Hz), 7.10 – 7.18(1H, m), 7.23 – 7.41(3H, m) | xi |
| 24 | Cl | Cl | Cl | C₂H₅ | 3,4-trans | IR(film): 1700cm⁻¹, NMR(CDCl₃)δ: 1.08(3H, t, J = 7.3Hz), 1.85 – 1.96(2H, m), 2.87 – 2.96(1H, m), 3.23(1H, dd, J = 9.7Hz, 6.5Hz), 3.43(1H, t, J = 9.7Hz), 3.76 – 3.93(1H, m), 4.40(1H, d, J = 14.9Hz), 4.56(1H, d, J = 14.9Hz), 4.63(1H, d, J = 6.5Hz), 7.10 – 7.29(1H, m), 7.20 – 7.32(3H, m) | xii |
| 25 | Cl | Cl | Cl | C₂H₅ | 3,4-cis | IR(film): 1700cm⁻¹, NMR(CDCl₃)δ: 1.08(3H, t, J = 7.6Hz), 1.51 – 1.63(1H, m), 1.65 – 1.88(1H, m), 2.71 – 2.81(1H, m), 3.07 – 3.43(2H, m), 4.04 – 4.13(1H, m), 4.33(1H, d, J = 14.9Hz), 4.56(1H, d, J = 5.4Hz), 4.60(1H, d, J = 14.9Hz), 7.10 – 7.14(1H, m), 7.22 – 7.35(3H, m) | xii |
| 26 | Br | Cl | Cl | C₂H₅ | Mixture of 3,4-cis and 3,4-trans | IR(film): 1700cm⁻¹, n_D 23.0° C: 1.5563 | xiii |
| 27 | Br | Cl | Cl | C₂H₅ | 3,4-trans | IR(film): 1700cm⁻¹, NMR(CDCl₃)δ: 1.08(3H, t, J = 7.3Hz), 1.91(2H, quint, J = 7.3Hz), 2.87 – 2.96(1H, m), 3.23(1H, dd, J = 9.6Hz, 6.1Hz), 3.43(1H, t, J = 9.6Hz), 3.87 – 3.93(1H, m), 4.40(1H, d, J = 14.9Hz), 4.54(1H, d, J = 14.9Hz), 4.63(1H, d, J = 6.9Hz), 7.16 – 7.26(2H, m), 7.40 – 7.46(2H, m) | xiv |
| 28 | Br | Cl | Cl | C₂H₅ | 3,4-cis | IR(film): 1700cm⁻¹, NMR(CDCl₃)δ: 1.08(3H, t, J = 7.3Hz), 1.51 – 1.77(2H, m), 2.71 – 2.83(1H, m), 3.10(1H, t, J = 9.3Hz), 3.19(1H, dd, J = 9.3Hz, 7.6Hz), 4.04 – 4.13(1H, m), 4.32(1H, d, J = 14.9Hz), 4.56(1H, d, J = 14.9Hz), 4.59(1H, d, J = 14.9Hz), 7.16 – 7.26(2H, m), 7.37 – 7.47(2H, m) | xiv |
| 29 | F | Cl | Cl | C₂H₅ | Mixture of 3,4-cis and 3,4-trans | IR(film): 1700cm⁻¹, n_D 20.2° C: 1.5142 | xv |
| 30 | F | Cl | Cl | C₂H₅ | 3,4-trans | IR(film): 1700cm⁻¹, n_D 20.4° C: 1.5020 | xvi |
| 31 | H | Cl | Cl | C₄H₉ | 3,4-trans | IR(film): 1700cm⁻¹, NMR(CDCl₃)δ: 0.90(3H, t, J = 7.6Hz), 1.23 – 1.73(6H, m), 2.69 – 2.80(1H, m), 3.23 – 3.44(2H, m), 4.14 – 4.21(1H, m), 4.41(1H, d, J = 14.9Hz), 4.55(1H, d, J = 8.9Hz), 4.62(1H, d, J = 14.9Hz), 7.22 – 7.29(2H, m), 7.31 – 7.40(3H, m) | xvii |
| 32 | H | Cl | Cl | C₄H₉ | 3,4-cis | IR(nujol): 1700cm⁻¹, NMR(CDCl₃)δ: 0.93(3H, t, J = 7.3Hz), 1.29 – 1.72(5H, m), 1.87 – 1.92(1H, m), 2.60 – 2.76(1H, m), 3.25(1H, dd, J = 10.5Hz, 9.5Hz), 3.45(1H, dd, J = 10.5Hz, 6.5Hz), 4.05 – 4.13(1H, m), 4.36(1H, d, J = 6.0Hz). | xvii |

TABLE 2-continued (I)

| Compound No. | Substituents of formula (I) | | | | Geometric isomerism | Physical properties | Source No. |
|---|---|---|---|---|---|---|---|
| | X | Y | Z | R | | | |
| 33 | H | Cl | Cl | C₄H₉ | 3,4-trans | 4.40(1H, d, J=14.9Hz), 4.60(1H, d, J=14.9Hz), 7.23–7.28(2H, m), 7.31–7.40(3H, m), m.p.: 53.0–55.0° C. | xviii |
| 34 | H | Cl | Cl | C₄H₉ | 3,4-cis | IR(film): 1700cm⁻¹, NMR(CDCl₃)δ: 0.91(3H, t, J=7.3Hz), 1.22–1.60(4H, m), 1.80–1.89(2H, m), 2.83–2.92(1H, m), 3.24(1H, dd, J=10.0Hz, 4.6Hz), 3.41(1H, dd, J=10.0Hz, 8.9Hz), 3.92–3.99(1H, m), 4.42(1H, d, J=14.9Hz), 4.60(1H, d, J=14.9Hz), 4.63(1H, d, J=6.5Hz), 7.23–7.28(2H, m), 7.30–7.39(3H, m) | xviii |
| 35 | Cl | Cl | Cl | C₄H₉ | 3,4-trans | IR(nujol): 1700cm⁻¹, NMR(CDCl₃)δ: 0.89(3H, t, J=7.3Hz), 1.14–1.62(6H, m), 2.68–2.82(1H, m), 3.09(1H, t, J=10.0Hz), 3.20(1H, dd, J=10.0Hz, 7.4Hz), 4.06–4.15(1H, m), 4.36(1H, d, J=14.9Hz), 4.55(1H, d, J=5.4Hz), 4.63(1H, d, J=14.9Hz), 7.22–7.29(2H, m), 7.31–7.40(3H, m), m.p.: 76.0–77.0° C. | xix |
| 36 | Cl | Cl | Cl | C₄H₉ | 3,4-cis | IR(film): 1700cm⁻¹, NMR(CDCl₃)δ: 0.91(3H, t, J=7.0Hz), 1.22–1.73(5H, m), 1.86–1.98(1H, m), 2.65–2.77(1H, m), 3.26(1H, t, J=10.0Hz), 3.45(1H, dd, J=10.0Hz, 7.3Hz), 4.06–4.11(1H, m), 4.36(1H, d, J=5.4Hz), 4.15–4.22(1H, m), 4.39(1H, d, J=14.9Hz), 4.56(1H, d, J=8.4Hz), 4.57(1H, d, J=14.9Hz), 7.12–7.15(1H, m), 7.24–7.31(1H, m) | xix |
| 37 | Cl | Cl | Cl | C₄H₉ | 3,4-trans | IR(film): 1700cm⁻¹, NMR(CDCl₃)δ: 0.92(3H, t, J=7.6Hz), 1.14–1.62(4H, m), 1.73–1.90(2H, m), 2.85–2.94(1H, m), 3.23(1H, dd, J=9.5Hz, 6.2Hz), 3.43(1H, t, J=9.5Hz), 3.95–4.00(1H, m), 4.41(1H, d, J=14.9Hz), 4.54(1H, d, J=14.9Hz), 4.38(1H, d, J=15.4Hz), 4.56(1H, d, J=15.4Hz), 7.12–7.15(1H, m), 7.23–7.39(3H, m) | xx |
| 38 | Cl | Cl | Cl | C₄H₉ | 3,4-cis | IR(film): 1700cm⁻¹, NMR(CDCl₃)δ: 0.90(3H, t, J=7.6Hz), 1.21–1.63(6H, m), 2.70–2.82(1H, m), 3.07–3.26(2H, m), 4.07–4.16(1H, m), 4.33(1H, d, J=14.9Hz), 4.55(1H, d, J=4.9Hz), 4.59(1H, d, J=14.9Hz), 7.11–7.14(1H, m), 7.21–7.30(3H, m) | xx |
| 39 | H | Br | Br | C₃H₇ | 3,4-trans | IR(film): 1700, 1420, 1260cm⁻¹, n_D 21.2° C.: 1.5346 | xxi |
| 40 | H | Br | Br | C₃H₇ | 3,4-cis | IR(KBr): 1600, 1440, 1420, 1270, 1170cm⁻¹, m.p.: 94.0–98.5° C. | xxi |
| 41 | H | Cl | Br | C₃H₇ | Mixture of 3,4-cis and 3,4-trans | IR(film): 1700, 1430, 1280, 1260cm⁻¹, n_D 21.0° C.: 1.5193 | xxii |

Synthetic example for important intermediate products for sythesizing the compound of the general formula (I) according to the present invention will be shown as reference examples.

In the same procedures, other intermediate acetamide derivatives were synthesized and compounds and physical properties are shown in Table 3.

TABLE 3

$$\text{(V)}$$

Structure: X-substituted phenyl ring with $-CH_2N(COCY_3)(CH_2CH=CHR)$

| Substituents of formula (V) | | | |
|---|---|---|---|
| X | Y | R | Physical properties |
| H | Cl | $C_2H_5$ | IR(film): 1675cm$^{-1}$, NMR(CDCl$_3$)δ: 0.85~1.05(3H, m), 1.82~2.00(2H, m), 4.22~4.35(2H, m), 4.55~4.70(2H, m), 5.30~5.47(1H, m), 5.60~5.75(1H, m), 7.08~7.30(5H, m), $n_D$24.7° C.: 1.4215 |
| Cl | Cl | $C_2H_5$ | IR(film): 1675cm$^{-1}$, $n_D$22.6° C.: 1.5142 |
| Br | Cl | $C_2H_5$ | IR(film): 1670cm$^{-1}$, $n_D$24.7° C.: 1.5260 |
| F | Cl | $C_2H_5$ | IR(film): 1675cm$^{-1}$, $n_D$22.4° C.: 1.4215 |
| H | Cl | $C_3H_7$ | IR(film): 1675cm$^{-1}$, $n_D$22.5° C.: 1.4862 |
| Cl | Cl | $C_3H_7$ | IR(film): 1675cm$^{-1}$, NMR(CDCl$_3$)δ: 0.94(3H, t, J=7.3Hz), 1.32~1.45(2H, m), 1.97~2.12(2H, m), 4.18~4.27(2H, m), 4.57~4.70(2H, m), 5.40~5.75(2H, m), 7.08~7.35(4H, m) |
| Br | Cl | $C_3H_7$ | IR(film): 1675cm$^{-1}$, NMR(CDCl$_3$)δ: 0.88(3H, t, J=7.0Hz), 1.35(2H, m), 2.02(2H, m), 4.18~4.27(2H, m), 4.57~4.70(2H, m), 5.40~5.75(2H, m), 7.18~7.50(4H, m) |
| F | Cl | $C_3H_7$ | IR(film): 1675cm$^{-1}$, $n_D$22.2° C.: 1.4521 |
| H | Cl | $C_4H_9$ | IR(film): 1675cm$^{-1}$, NMR(CDCl$_3$)δ: 0.86(3H, t, J=7.3Hz), 1.21~1.56(4H, m), 2.00~2.10(2H, m), 4.15~4.25(2H, m), 4.60~4.70(2H, m), 5.40~5.70(2H, m), 7.20~7.37(5H, m) |
| Cl | Cl | $C_4H_9$ | IR(film): 1675cm$^{-1}$, NMR(CDCl$_3$)δ: 0.87(3H, t, J=7.4Hz), 1.20~1.56(4H, m), 2.00~2.10(2H, m), 4.17~4.26(2H, m), 4.62~4.70(2H, m), 5.40~5.51(1H, m), 5.53~5.70(1H, m), 7.16~7.33(4H, m) |
| H | Br | $C_3H_7$ | IR(film):1680cm$^{-1}$, NMR(CDCl$_3$)δ: 0.93(3H, t, J=7.4Hz), 1.31~1.45(2H, m), 1.95~2.15(2H, m), 4.18~4.27(2H, m), 4.55~4.72(2H, m), 5.40~5.75(2H, m), 7.10~7.35(5H, m) |

REFERENCE EXAMPLE 1

Synthesis for N-(3-chlorobenzyl)-N-(2-pentenyl)-2,2-dichloroacetamide 2 g of N-(3-chlorobenzyl)-N-(2-heptenyl)amine was dissolved in 40 ml of toluene, to which 1.7 g of 2,2-dichloroacetyl chloride was dropped under stirring gradually at a room temperature. After stirring for 20 min, deposited insoluble matters were filtered and then 50 ml of toluene was added. The toluene solution was washed with an aqueous saturated solution of sodium hydrogen carbonate and with a saturated solution of sodium chloride respectively each by twice. After dying with anhydrous sodium sulfate, it was concentrated in an evaporated to obtain an aimed oily product quantitatively.

IR (film): 1665 cm$^{-1}$.
$n_D$22.0° C.: 1.5085.

REFERENCE EXAMPLE 2

Synthesis for N-benzyl-N-(2-heptenyl)amine 13 g of potassium carbonate and 20 g of benzylamine were added to 25 ml of N,N-dimethylformamide and, further, 20 g of 2-hexenyl chloride was added and stirred at 100°–120° C. for one hour. After the reaction, 100 ml of an aqueous solution of sodium chloride was added, extracted with ethyl acetate and dried with anhydrous sodium sulfate. After concentration in an evaporator, it was subjected to silica gel column chromatography (hexane/ethyl acetate=1/1, v/v) to obtain 18 g of the aimed compound.

IR (film): 2950, 1445 cm$^{-1}$.

NMR (CDCl$_3$) δ: 0.91 (3H,t,J=7.6Hz), 1.29–1.50 (2H,m), 1.95–1.06 (2H, m), 3.15–3.23 (2H, m), 3.75 (2H,s), 5.46–5.66 (2H,m), 7.20–7.35 (5H,m).

Yield: 51.0%.

In the same procedures, other intermediate alkenylamine derivatives were synthesized and the compounds and their physical property are shown in Table 4.

TABLE 4

$$\text{(III)}$$

Structure: X-substituted phenyl ring with $-CH_2NHCH_2CH=CHR$

| Substituents of formula (III) | | |
|---|---|---|
| X | R | Physical properties |
| H | $C_2H_5$ | IR(film): 2960, 1445cm$^{-1}$, NMR(CDCl$_3$)δ: 0.94(3H, t, J=7.5Hz), 1.92~2.08(2H, m), 3.16~3.22(2H, m), 3.74(2H, s), 5.47~5.66(2H, m), 7.20~7.35(5H, m) |

TABLE 4-continued $$\text{(III)} \quad \underset{X}{\bigcirc}-CH_2NHCH_2CH=CHR$$

| Substituents of formula (III) | | |
|---|---|---|
| X | R | Physical properties |
| Cl | $C_2H_5$ | IR(film): 2960, 1445cm$^{-1}$, NMR(CDCl$_3$)δ: 0.95(3H, t, J=7.5Hz), 1.93~2.10(2H, m), 3.17~3.24(2H, m), 3.75(2H, s), 5.47~5.66(2H, m), 7.16~7.34(4H, m) |
| Br | $C_2H_5$ | IR(film): 2950, 1585, 1560, 1445, 1420cm$^{-1}$, n$_D$ 25.4° C.: 1.4215 |
| F | $C_2H_5$ | IR(film): 2950, 1445cm$^{-1}$, NMR(CDCl$_3$)δ:0.97(3H, t, J=7.6Hz), 2.10(2H, m), 3.30(2H, d, J=6.0Hz),3.80(2H, s), 5.50(2H, m), 6.94(1H, m), 7.00(2H, t, J=7.0Hz), 7.27(1H, m), n$_D$ 22.4° C.: 1.4215 |
| Cl | $C_3H_7$ | IR(film): 2950, 1445cm$^{-1}$, NMR(CDCl$_3$)δ: 0.90(3H, t, J=7.6Hz), 1.30~1.50(2H, m), 1.95~2.05(2H, m), 3.17~3.23(2H, m), 3.75(2H, s), 5.47~5.67(2H, m), 7.16~7.34(4H, m) |
| Br | $C_3H_7$ | IR(film): 2950, 1585, 1560, 1445, 1420cm$^{-1}$, NMR(CDCl$_3$)δ: 0.90(3H, t, J=7.6Hz), 1.30~1.50(2H, m), 1.95~2.05(2H, m), 3.20(2H, m), 3.75(2H, s), 5.47~5.67(2H, m), 7.16~7.50(4H, m) |
| F | $C_3H_7$ | IR(film): 2950, 1590, 1450, 1250cm$^{-1}$, NMR(CDCl$_3$)δ: 0.90(3H, t, J=7.6Hz), 1.29~1.50(2H, m), 2.01(2H, m), 3.20(2H, d, J=6.0Hz), 3.78(2H, s), 5.49~5.65(2H, m), 6.95(1H, m), 7.00(2H, t, J=7.0Hz), 7.27(1H, m) |
| H | $C_4H_9$ | IR(film): 2955, 1445cm$^{-1}$, NMR(CDCl$_3$)δ: 0.89(3H, t, J=7.6Hz), 1.25~1.40(4H, m), 1.97~2.07(2H, m), 3.20~3.24(2H, m), 3.80(2H, s), 5.47~5.66(2H, m), 7.20~7.35(5H, m) |
| Cl | $C_4H_9$ | IR(film): 2955, 1445cm$^{-1}$, NMR(CDCl$_3$)δ: 0.90(3H, t, J=7.6Hz), 1.25~1.40(4H, m), 1.95~2.05(2H, m), 3.21~3.25(2H, m), 3.79(2H, s), 5.36~5.65(2H, m), 7.16~7.34(4H, m) |

FORMULATION EXAMPLES AND TEST EXAMPLES

Then, formulation examples and test examples for the herbicidal activity of the herbicide according to the present invention are described below.

FORMULATION EXAMPLE 1 (WETTABLE POWDER)

A wettable powder was prepared by sufficiently pulverizing and mixing 20 parts by weight of the compound (1) of the present invention, 2 parts by weight of Neopelax (trade name of product: sodium dodecylbenzene sulfonate, manufactured by Kao Atlas Co.), 2 parts by weight of Neugen EA (trade name of products: polyoxyethylene nonyl phenyl ether, manufactured by Daiichi Kogyo Seiyaku, Co.), 5 parts by weight of white carbon and 71 parts by weight of diatomaceous earth.

FORMULATION EXAMPLE 2 (DUST)

A dust was prepared by sufficiently pulverizing and mixing 1 parts by weight of the compound (3) according to the present invention, 0.5 parts by weight of Emulgen 910 (trade name of product: polyoxyethylene nonyl phenyl ether, manufactured by Kao Co.) and 98.5 parts by weight of kaoline clay.

FORMULATION EXAMPLE 3 (GRANULE)

After sufficiently mixing 1 parts by weight of the finely powderized compound (3) according to the present invention, 2 parts by weight of Neopelex (trade name as described above), 2 parts by weight of Sunex P252 (trade name of product: sodium lignin sulfonate, manufactured by Sanyo Kokusaku Pulp Co.) and 72 parts by weight of bentonite and 23 parts by weight of talc, they were wetted with addition of an appropriate amount of water and then extruded by a small injection molding machine for pelletization. After air drying and crushing them at 30°–60° C., they were pelletized by a granulator into 0.3–2 mm size to obtain granules.

FORMULATION EXAMPLE 4 (EMULSIFIABLE CONCENTRATE)

An emulsifiable concentrate was prepared by mixing and dissolving 10 parts by weight of the compound (7) according to the present invention, 10 parts by weight of Solpol 800A (trade name of product: a mixture of nonionic surface active agent and anionic surface active agent, manufactured by Toho Kagaku Co.) and 80 parts by weight of o-xylene.

FORMULATION EXAMPLE 5 (FLOWABLE AGENT)

A flowable agent was obtained by wet pulverizing and mixing 30 parts by weight of of the compound (34) according to the present invention and 10 parts by weight of Sunex 252 P (trade name of products as described above) dissolved in 50 parts by weight of water and, subsequently and adding and mixing 0.2 parts by weight of Kerzan S (trade name of products xanthane gum, manufactured by Kerco Co.) and 0.2 parts by weight of Deltop (trade name of products of organic iodine type antifungus agent, manufactured by Takeda Yakuhin Kogyo Co.) dissolved in 9.6 by weight of water.

TEST EXAMPLE 1 FLOODE SOIL TREATMENT TEST (PRE-EMERGENCE TREATMENT)

Soils were packed into each of 1/5000 are Wagner pots, to which seeds or tuber roots of *Echinochloa crusgalli, Scirpus juncoides, Cyperus serotinus, Monochoria vaginalis* and other annual broad leaf weeds were seeded and put into a flooded condition. Previously grown seedlings of paddy field rice (2–3 leaf stage) were collected each by two into one hill and two hills were transplanted into each pot and caused to grow in a greenhouse. One day after (before emergence of weeds), they were treated by using the granule prepared from a predetermined amount of the tested compound in accordance with the method as described in the Formulation Example 3, and the state of growth of weeds and the state of phytotoxicity to the paddy rice plant were observed and investigated after 30 days. The results are shown in Table 5.

In the table, the degree of injury to the tested plants and the degree of phytotoxicity to paddy field rice were indicated based on the following standards by the growing state of the plants in comparison with a not-treated case, based on the air-dried weight.

| Indication | Growing rate (%) shown by the ratio of air-dry weight based on not-treated lot | |
|---|---|---|
| 5 | 0-5 | (dead) |
| 4 | 6-10 | (severe damage) |
| 3 | 11-40 | (medium damage) |
| 2 | 41-70 | (less damage) |
| 1 | 71-90 | (slight damage) |
| 0 | 91-100 | (no damage) |

The known comparative compounds A, B, C, D, E, F and G represent the following compounds (also in Test Example 2 described later).

A: 3-chloro-4-chloromethyl-1-(3-trifluoromethylphenyl)-2-pyrrolidinone (common name: fluorochloridone)
B: 1-benzyl-3-chloro-4-chloromethyl-2-pyrrolidinone
C: 1-(4-chlorobenzyl)-3-chloro-4-chloromethyl-2-pyrrolidinone
D: S-(4-chlorobenzyl)-N,N-diethylthiol carbamate (common name: benthiocarb)
E: 3-chloro-4-chloromethyl-1-(2,6-diethylphenyl)-2-pyrrolidinone
F: 1-allyl-3-chloro-4-chloromethyl-2-pyrrolidinone
G: 3-bromo-4-bromomethyl-1-(3-chlorophenyl)-2-pyrrolidinone

TABLE 5

| | | Test in flooded soil (Pre-emergence treatment) | | | | | |
|---|---|---|---|---|---|---|---|
| Compound No. | Dosage Kg/ha | Echinochloa crusgalli | Annual broad leaves | Monochoria vaginalis | Scirpus juncoides | Cyperus serotinus | Paddy rice |
| 1 | 0.3 | 4 | 2 | 3 | 2 | 1 | 0 |
| | 0.6 | 5 | 4 | 4 | 3 | 3 | 0 |
| | 1.2 | 5 | 5 | 5 | 4 | 4 | 0 |
| 3 | 0.3 | 5 | 4 | 5 | 3 | 2 | 0 |
| | 0.6 | 5 | 5 | 5 | 5 | 4 | 0 |
| | 1.2 | 5 | 5 | 5 | 5 | 5 | 0 |
| 5 | 0.3 | 5 | 5 | 4 | 4 | 2 | 0 |
| | 0.6 | 5 | 5 | 5 | 5 | 5 | 0 |
| | 1.2 | 5 | 5 | 5 | 5 | 5 | 1 |
| 7 | 0.3 | 5 | 3 | 4 | 2 | 1 | 0 |
| | 0.6 | 5 | 4 | 5 | 4 | 2 | 0 |
| | 1.2 | 5 | 5 | 5 | 5 | 4 | 0 |
| 9 | 0.3 | 5 | 4 | 5 | 3 | 1 | 0 |
| | 0.6 | 5 | 4 | 5 | 5 | 3 | 0 |
| | 1.2 | 5 | 5 | 5 | 5 | 5 | 0 |
| 11 | 0.3 | 5 | 3 | 3 | 2 | 2 | 0 |
| | 0.6 | 5 | 4 | 5 | 4 | 4 | 0 |
| | 1.2 | 5 | 5 | 5 | 5 | 5 | 0 |
| 13 | 0.3 | 5 | 4 | 4 | 3 | 1 | 0 |
| | 0.6 | 5 | 4 | 5 | 4 | 3 | 0 |
| | 1.2 | 5 | 5 | 5 | 5 | 4 | 0 |
| 15 | 0.3 | 5 | 3 | 5 | 3 | 2 | 0 |
| | 0.6 | 5 | 4 | 5 | 5 | 3 | 0 |
| | 1.2 | 5 | 5 | 5 | 5 | 4 | 0 |
| 17 | 0.3 | 5 | 4 | 5 | 3 | 2 | 0 |
| | 0.6 | 5 | 4 | 5 | 5 | 4 | 0 |
| | 1.2 | 5 | 5 | 5 | 5 | 4 | 0 |
| 19 | 0.3 | 5 | 4 | 4 | 4 | 2 | 0 |
| | 0.6 | 5 | 4 | 5 | 5 | 4 | 0 |
| | 1.2 | 5 | 5 | 5 | 5 | 5 | 0 |
| 21 | 0.3 | 5 | 5 | 5 | 5 | 2 | 0 |
| | 0.6 | 5 | 5 | 5 | 5 | 3 | 0 |
| | 1.2 | 5 | 5 | 5 | 5 | 4 | 1 |
| 23 | 0.3 | 5 | 3 | 5 | 3 | 3 | 0 |
| | 0.6 | 5 | 4 | 5 | 4 | 4 | 0 |
| | 1.2 | 5 | 5 | 5 | 5 | 5 | 0 |
| 25 | 0.3 | 5 | 4 | 5 | 4 | 2 | 0 |
| | 0.6 | 5 | 4 | 5 | 4 | 3 | 0 |
| | 1.2 | 5 | 5 | 5 | 5 | 4 | 0 |
| 26 | 0.3 | 4 | 3 | 3 | 2 | 1 | 0 |
| | 0.6 | 5 | 4 | 5 | 4 | 2 | 0 |
| | 1.2 | 5 | 5 | 5 | 5 | 4 | 0 |
| 28 | 0.3 | 4 | 4 | 4 | 3 | 2 | 0 |
| | 0.6 | 5 | 4 | 5 | 5 | 3 | 0 |
| | 1.2 | 5 | 5 | 5 | 5 | 4 | 0 |
| 29 | 0.3 | 4 | 3 | 3 | 2 | 2 | 0 |
| | 0.6 | 5 | 4 | 4 | 3 | 3 | 0 |
| | 1.2 | 5 | 5 | 5 | 4 | 4 | 0 |
| 30 | 0.3 | 5 | 3 | 4 | 3 | 2 | 0 |

TABLE 5-continued

Test in flooded soil (Pre-emergence treatment)

| Compound No. | Dosage Kg/ha | Echinochloa crusgalli | Annual broad leaves | Monochoria vaginalis | Scirpus juncoides | Cyperus serotinus | Paddy rice |
|---|---|---|---|---|---|---|---|
| | 0.6 | 5 | 4 | 5 | 4 | 3 | 0 |
| | 1.2 | 5 | 5 | 5 | 5 | 4 | 0 |
| 32 | 0.3 | 5 | 3 | 4 | 3 | 2 | 0 |
| | 0.6 | 5 | 4 | 5 | 4 | 4 | 0 |
| | 1.2 | 5 | 5 | 5 | 5 | 5 | 0 |
| 34 | 0.3 | 5 | 3 | 5 | 3 | 2 | 0 |
| | 0.6 | 5 | 4 | 5 | 4 | 3 | 0 |
| | 1.2 | 5 | 5 | 5 | 5 | 4 | 0 |
| 36 | 0.3 | 5 | 3 | 4 | 2 | 1 | 0 |
| | 0.6 | 5 | 4 | 5 | 3 | 2 | 0 |
| | 1.2 | 5 | 4 | 5 | 4 | 4 | 0 |
| 38 | 0.3 | 5 | 3 | 4 | 3 | 1 | 0 |
| | 0.6 | 5 | 4 | 5 | 4 | 3 | 0 |
| | 1.2 | 5 | 5 | 5 | 5 | 4 | 0 |
| 40 | 0.3 | 5 | 2 | 4 | 2 | 1 | 0 |
| | 0.6 | 5 | 3 | 5 | 3 | 3 | 0 |
| | 1.2 | 5 | 4 | 5 | 4 | 4 | 0 |
| 41 | 0.3 | 4 | 2 | 4 | 2 | 1 | 0 |
| | 0.6 | 5 | 3 | 5 | 4 | 3 | 0 |
| | 1.2 | 5 | 4 | 5 | 5 | 5 | 0 |
| A | 0.3 | 3 | 3 | 3 | 4 | 3 | 4 |
| | 0.6 | 5 | 4 | 5 | 5 | 4 | 5 |
| | 1.2 | 5 | 5 | 5 | 5 | 5 | 5 |
| B | 0.3 | 0 | 0 | 0 | 0 | 0 | 0 |
| | 0.6 | 2 | 0 | 1 | 0 | 0 | 2 |
| | 1.2 | 4 | 1 | 2 | 0 | 0 | 3 |
| C | 0.3 | 0 | 0 | 0 | 0 | 0 | 0 |
| | 0.6 | 1 | 0 | 1 | 0 | 0 | 1 |
| | 1.2 | 3 | 1 | 3 | 2 | 1 | 3 |
| D | 0.3 | 1 | 0 | 0 | 0 | 0 | 0 |
| | 0.6 | 3 | 0 | 1 | 0 | 1 | 0 |
| | 1.2 | 5 | 1 | 2 | 1 | 1 | 0 |
| E | 0.3 | 0 | 0 | 0 | 0 | 0 | 0 |
| | 0.6 | 0 | 0 | 0 | 0 | 0 | 0 |
| | 1.2 | 0 | 0 | 0 | 0 | 0 | 0 |
| F | 0.3 | 0 | 0 | 0 | 0 | 0 | 0 |
| | 0.6 | 0 | 0 | 0 | 0 | 0 | 0 |
| | 1.2 | 0 | 0 | 0 | 0 | 0 | 0 |
| G | 0.3 | 0 | 0 | 0 | 0 | 0 | 0 |
| | 0.6 | 0 | 1 | 0 | 0 | 0 | 0 |
| | 1.2 | 2 | 3 | 1 | 1 | 0 | 0 |

In this test, the control compound A showed a strong chlorosis and exhibited substantially complete herbicidal effect by treatment with 0.6 kg/ha, but it also gave remarkable phytotoxicity also to paddy field rice.

For the control compounds B and C, although growth controlling effect was observed by treatment with 1.2 kg/ha, the effect by the treatment with lower dosage was poor.

The control compound D showed herbicidal effect against *Echinochloa crusgalli* by treatment with 1.2 kg/ha and no phytotoxicity was observed to paddy field rice, but the effect by treatment at a dosage of less than 0.6 kg/ha was insufficient.

The control compounds E, F and G scarcely showed activity to all of weed species by the treatment with 1.2 kg/ha.

On the other hand, the compound according to the present invention showed satisfactory weed controlling effect (due to growth controlling effect) even at a low dosage and phytotoxicity to the paddy field rice plant was scarcely observed. In particular, it exhibited substantially sufficient controlling effect against *Echinochloa crusgalli* by treatment with 0.3 kg/ha.

TEST EXAMPLE 2 FLOODED SOIL TREATMENT TEST (GROWING STAGE TREATMENT)

Soils were packed into each of 1/5000 are Wagner pots to which seeds or tuber roots of *Echinochloa crusgalli Scirpus juncoides, Cyperus serotinus, Monochoaria vaginalis* and other annual broad leaf weeds were seeded and put into a flooded condition. Previously grown seedlings of paddy field rice (2-3 leaf stage) were collected each by two into one hill and two hills were transplanted into each pot and caused to grow in a greenhouse. When *Echinochloa crusgalli* grew into the 2-leaf stage, treatment was applied by using the granule prepared from a predetermined amount of the tested compound in accordance with the method as described in the Formulation Example 3, and the state of emergence of weeds was observed and investigated after 30 days.

The results are shown in Table 6.

In the table, the degree of injury to the tested plants and the degree of phytotoxicity to the crop were indicated in the same manner as in Test Example 1.

TABLE 6

| Compound No | Dosage Kg/ha | Echinochloa crusgalli | Annual broad leaves | Monochoria vaginalis | Scirpus juncoides | Cyperus serotinus | Paddy rice |
|---|---|---|---|---|---|---|---|
| 1 | 0.5 | 3 | 2 | 2 | 1 | 0 | 0 |
|   | 1.0 | 4 | 3 | 3 | 2 | 1 | 0 |
|   | 2.0 | 5 | 4 | 5 | 2 | 2 | 0 |
| 3 | 0.5 | 5 | 3 | 3 | 1 | 1 | 0 |
|   | 1.0 | 5 | 3 | 4 | 2 | 2 | 0 |
|   | 2.0 | 5 | 5 | 5 | 3 | 3 | 0 |
| 5 | 0.5 | 5 | 3 | 2 | 1 | 0 | 0 |
|   | 1.0 | 5 | 4 | 4 | 2 | 2 | 0 |
|   | 2.0 | 5 | 5 | 5 | 3 | 3 | 0 |
| 7 | 0.5 | 5 | 2 | 2 | 1 | 0 | 0 |
|   | 1.0 | 5 | 4 | 4 | 2 | 2 | 0 |
|   | 2.0 | 5 | 5 | 5 | 3 | 3 | 0 |
| 9 | 0.5 | 5 | 3 | 3 | 1 | 1 | 0 |
|   | 1.0 | 5 | 4 | 4 | 2 | 2 | 0 |
|   | 2.0 | 5 | 5 | 5 | 3 | 3 | 0 |
| 11 | 0.5 | 5 | 2 | 2 | 1 | 0 | 0 |
|   | 1.0 | 5 | 3 | 3 | 2 | 1 | 0 |
|   | 2.0 | 5 | 4 | 5 | 3 | 2 | 0 |
| 13 | 0.5 | 5 | 2 | 3 | 1 | 0 | 0 |
|   | 1.0 | 5 | 4 | 4 | 1 | 1 | 0 |
|   | 2.0 | 5 | 4 | 5 | 2 | 2 | 0 |
| 15 | 0.5 | 5 | 2 | 3 | 1 | 0 | 0 |
|   | 1.0 | 5 | 3 | 4 | 1 | 0 | 0 |
|   | 2.0 | 5 | 4 | 5 | 2 | 2 | 0 |
| 17 | 0.5 | 5 | 2 | 4 | 1 | 1 | 0 |
|   | 1.0 | 5 | 3 | 5 | 2 | 1 | 0 |
|   | 2.0 | 5 | 5 | 5 | 3 | 3 | 0 |
| 19 | 0.5 | 5 | 3 | 4 | 0 | 0 | 0 |
|   | 1.0 | 5 | 4 | 5 | 2 | 1 | 0 |
|   | 2.0 | 5 | 5 | 5 | 3 | 2 | 0 |
| 21 | 0.5 | 5 | 4 | 3 | 1 | 0 | 0 |
|   | 1.0 | 5 | 4 | 4 | 2 | 2 | 0 |
|   | 2.0 | 5 | 5 | 5 | 2 | 3 | 0 |
| 23 | 0.5 | 5 | 2 | 4 | 1 | 0 | 0 |
|   | 1.0 | 5 | 3 | 5 | 1 | 1 | 0 |
|   | 2.0 | 5 | 5 | 5 | 2 | 2 | 0 |
| 25 | 0.5 | 5 | 2 | 3 | 0 | 0 | 0 |
|   | 1.0 | 5 | 4 | 4 | 1 | 1 | 0 |
|   | 2.0 | 5 | 5 | 5 | 2 | 2 | 0 |
| 26 | 0.5 | 4 | 2 | 2 | 0 | 0 | 0 |
|   | 1.0 | 4 | 3 | 3 | 1 | 0 | 0 |
|   | 2.0 | 5 | 3 | 5 | 2 | 1 | 0 |
| 28 | 0.5 | 4 | 2 | 3 | 0 | 0 | 0 |
|   | 1.0 | 5 | 3 | 4 | 1 | 0 | 0 |
|   | 2.0 | 5 | 4 | 5 | 1 | 1 | 0 |
| 29 | 0.5 | 4 | 2 | 3 | 0 | 0 | 0 |
|   | 1.0 | 5 | 3 | 4 | 1 | 0 | 0 |
|   | 2.0 | 5 | 5 | 5 | 2 | 1 | 0 |
| 30 | 0.5 | 4 | 2 | 2 | 0 | 0 | 0 |
|   | 1.0 | 4 | 4 | 3 | 1 | 0 | 0 |
|   | 2.0 | 5 | 5 | 5 | 2 | 1 | 0 |
| 32 | 0.5 | 5 | 2 | 3 | 0 | 0 | 0 |
|   | 1.0 | 5 | 3 | 4 | 1 | 1 | 0 |
|   | 2.0 | 5 | 4 | 5 | 3 | 2 | 0 |
| 34 | 0.5 | 5 | 2 | 3 | 1 | 1 | 0 |
|   | 1.0 | 5 | 4 | 4 | 1 | 2 | 0 |
|   | 2.0 | 5 | 5 | 5 | 3 | 2 | 0 |
| 36 | 0.5 | 5 | 2 | 2 | 1 | 0 | 0 |
|   | 1.0 | 5 | 3 | 4 | 2 | 2 | 0 |
|   | 2.0 | 5 | 4 | 5 | 3 | 2 | 0 |
| 38 | 0.5 | 5 | 2 | 4 | 0 | 0 | 0 |
|   | 1.0 | 5 | 4 | 5 | 2 | 1 | 0 |
|   | 2.0 | 5 | 5 | 5 | 3 | 2 | 0 |
| 40 | 0.5 | 5 | 2 | 3 | 0 | 0 | 0 |
|   | 1.0 | 5 | 3 | 4 | 1 | 1 | 0 |
|   | 2.0 | 5 | 4 | 5 | 3 | 2 | 0 |
| 41 | 0.5 | 3 | 2 | 3 | 0 | 0 | 0 |
|   | 1.0 | 4 | 4 | 4 | 1 | 1 | 0 |
|   | 2.0 | 5 | 4 | 5 | 2 | 1 | 0 |
| A | 0.5 | 2 | 2 | 2 | 1 | 2 | 4 |
|   | 1.0 | 5 | 4 | 5 | 4 | 4 | 5 |
|   | 2.0 | 5 | 5 | 5 | 5 | 5 | 5 |
| B | 0.5 | 0 | 0 | 0 | 0 | 0 | 0 |
|   | 1.0 | 1 | 1 | 1 | 0 | 0 | 2 |
|   | 2.0 | 2 | 3 | 2 | 0 | 0 | 2 |
| C | 0.5 | 0 | 0 | 0 | 0 | 0 | 0 |
|   | 1.0 | 0 | 0 | 1 | 0 | 0 | 1 |
|   | 2.0 | 3 | 2 | 2 | 0 | 0 | 2 |

TABLE 6-continued

| | | Test in flooded soil (Post-emergence treatment) | | | | | |
|---|---|---|---|---|---|---|---|
| Compound No | Dosage Kg/ha | Echinochloa crusgalli | Annual broad leaves | Monochoria vaginalis | Scirpus juncoides | Cyperus serotinus | Paddy rice |
| D | 0.5 | 1 | 0 | 0 | 0 | 0 | 0 |
| | 1.0 | 2 | 1 | 0 | 0 | 1 | 0 |
| | 2.0 | 5 | 3 | 2 | 0 | 1 | 0 |
| E | 0.5 | 0 | 0 | 0 | 0 | 0 | 0 |
| | 1.0 | 0 | 0 | 0 | 0 | 0 | 0 |
| | 2.0 | 0 | 0 | 0 | 0 | 0 | 0 |
| F | 0.5 | 0 | 0 | 0 | 0 | 0 | 0 |
| | 1.0 | 0 | 0 | 0 | 0 | 0 | 0 |
| | 2.0 | 0 | 0 | 0 | 0 | 0 | 0 |
| G | 0.5 | 0 | 0 | 0 | 0 | 0 | 0 |
| | 1.0 | 0 | 0 | 0 | 0 | 0 | 0 |
| | 2.0 | 1 | 2 | 1 | 1 | 0 | 0 |

In this test, the control compound A showed a strong chlorosis and exhibited substantially complete herbicidal effect by treatment with 1.0 kg/ha, but it also gave remarkable phytotoxicity also to paddy field rice.

For the control compound B and C only showed extremely weak grow controlling effect by treatment with 2.0 kg/ha not attaining weed killing.

The control compound D showed herbicidal effect against Echinochloa crusgalli by treatment with 1.0-2.0 kg/ha and no phytotoxicity was observed to paddy field rice, but the effect by treatment at a dosage of less than 1.0 kg/ha was insufficient.

The control compounds E, F and G scarcely showed activity to all of weed species by the treatment with 2.0 kg/ha.

On the other hand, the compound according to the present invention was poor in the controlling effect against perennial weeds but showed substantially complete controlling effect against Echinochloa crusgalli by treatment with 0.5 kg/ha and phytotoxicity to the paddy fields rice plant was not observed.

The compound according to the present invention has remarkably increased herbicidal effect against paddy field weeds as compared with known compounds and, in particular, has a feature of exhibiting herbicidal effect, against Echinochloa crusgalli which is one of important weeds, with an extremely less dosage, for a longer period of time from the pre-emergence stage to the growing stage. Meanwhile, since the compound scarcely shows phytotoxicity to the paddy field rice plant, it has a high applicability as a paddy field rice herbicide and can be used with extreme safety.

What is claimed is:

1. A 3,4-cis 1-(3-substituted benzyl)-3-halogeno-4-(1-halogenoalkyl)-2-pyrrolidinone represented by the general formula (I):

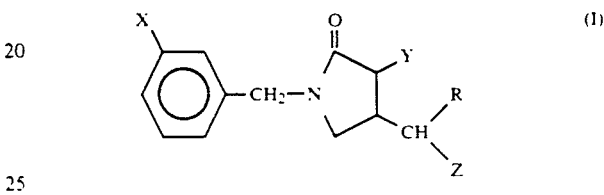

where X represents a hydrogen atom or chlorine atom, Y and Z each represents a chlorine atom and R represents an alkyl group with 2 to 4 carbon atoms.

2. The 3,4-cis isomer of a compound of claim 1, substantially free from the 3,4-trans isomer.

3. A compound of claim 1, wherein Y and Z both are Cl.

4. A compound of claim 1, wherein X is H, Cl or F.

5. A compound of claim 1, wherein R is $C_2H_5$ or n—$C_3H_7$.

6. A compound of claim 2, wherein Y and Z both are Cl, X is H, Cl or F and R is $C_2H_5$ or n—$C_3H_7$.

7. 1-Benzyl-4-(1-chlorobutyl)-3-chloro-2-pyrrolidinone, a compound of claim 1.

8. 1-(3-Chlorobenzyl)-4-(1-chlorobutyl)-3-chloro-2-pyrrolidinone, a compound of claim 1.

9. A herbicidal composition containing, in admixture with a carrier, a herbicidally effective amount of a compound of claim 1.

10. A herbicidal composition according to claim 9, wherein the compound of formula (I) is present therein as the 3,4-cis isomer thereof, substantially free from the 3,4-trans isomer.

11. A herbicidal composition according to claim 9, wherein in the compound of formula (I) Y and Z both are Cl.

12. A herbicidal composition according to claim 9, wherein in the compound of formula (I) X is H, Cl or F.

13. A herbicidal composition according to claim 9, wherein in the compound of formula (I) Y and Z both are Cl, X is H, Cl or F and R is $C_2H_5$ or n—$C_3H_7$.

14. A herbicidal composition according to claim 9, wherein the compound of formula (I) is 1-benzyl-4-(1-chlorobutyl)-3-chloro-2-pyrrolidinone.

15. A herbicidal composition according to claim 9, wherein the compound of formula (I) is 1-(3-chlorobenzyl)-4-(1-chlorobutyl)-3-chloro-2-pyrrolidinone.

* * * * *